United States Patent [19]

Kessler et al.

[11] Patent Number: 4,613,587
[45] Date of Patent: Sep. 23, 1986

[54] OPHTHALMIC PREPARATIONS

[75] Inventors: Efrat Kessler, Tel-Aviv; Abraham Spierer, Bne Braq; Shmaryahum Blumberg, Rishon Lezion, all of Israel

[73] Assignees: Yeda Research and Development Co. Ltd., Rehovot; Ramot University Authority for Applied Research and Industrial Development Ltd., Tel-Aviv, both of Israel

[21] Appl. No.: 628,724

[22] Filed: Jul. 10, 1984

[30] Foreign Application Priority Data

Sep. 23, 1983 [IL] Israel ................................... 69795

[51] Int. Cl.$^4$ ............................................ A61K 37/02
[52] U.S. Cl. ................................................... 514/19
[58] Field of Search .................... 260/112.5 R; 514/19

[56] References Cited

PUBLICATIONS

Metabolic Pediatric and Systemic Ophthalmology, vol. 6, 331–6 (1982).
Infection & Immunity, (1982) 716–23 vol. 38.
Advances in Biochem. Psychopharmacology, vol. 33, pp. 261-270.
Current Eye Research, vol. 3, (1984) 645–650.
Chem. Abstr. vol. 99, (1983) 102029c.
Chem. Abstr. vol. 98, (1983) 27344a.
Chem. Abstr. vol. 97, (1982) 158604n.
Chem. Abstr. vol. 101, (1984) 16850s.
Chem. Abstr. vol. 100, (1984) 2646x.

*Primary Examiner*—Delbert R. Phillips
*Attorney, Agent, or Firm*—Stiefel, Gross, Kurland & Pavane

[57] ABSTRACT

There are provided ophthalmic preparations against eye diseases caused by *P. aeruginosa* elastase or similar enzymes. The active ingredient is a 2-mercaptoacyl di- or tri-peptide obtained from suitable amino acids. There is further provided a process for the treatment of Pseudomonas keratitis by means of such compositions.

12 Claims, No Drawings

OPHTHALMIC PREPARATIONS

FIELD OF THE INVENTION

The invention relates to pharmaceutical compositions containing as active ingredient 2-mercapto-acetyl di- and tripeptides. The pharmaceutical compositions are ophthalmic preparations, to be used against agents releasing metalloendopeptidases, and especially by the enzyme of *Pseudomonas aeruginosa* which is the agent causing pseudomonas keratitis.

BACKGROUND OF THE INVENTION

In 1961, typical necrotizing vasculitis occuring in tissues of patients with infectious processes due to *Pseudomonas aeruginosa* was recognized. These were recognized in 1965 to be associated with the elastase of these bacteria. Since that time there have been numerous publications on the elastase of *P. aeruginosa*. The elastase of *P. aeruginosa* was crystallized and it was found to contain 0.9 gram atom zinc per mole of the enzyme, which is essential to the enzymatic activity. The elastase has a molecular weight of about 35.000. It is most active in the neutral pH range and it is known to be inactivated by various metal chelators, the zinc being an essential component for its activity.

The elastase is inhibited by EDTA and O-phenanthroline. Certain peptide hydroxamic acids are effective inhibitors for this elastase. The known inhibitors are effective at rather large concentrations. According to the present invention there are provided highly specific inhibitors which are effective at very low concentrations and which can be used as the active ingredient in pharmaceutical, and especially ophthalmic compositions for the prevention of, and for the treatment of afflictions of the human eye by *P. aeruginosa* and for the treatment of other diseases caused by this microorganism or by microorganisms which produce a similar enzyme.

SUMMARY OF THE INVENTION

The present invention relates to novel pharmaceutical ophthalmic preparations based on certain 2-mercaptoacyl dipeptides and tripeptides.

The dipeptides and tripeptides are based on the one hand on the mercaptoacyl moiety adapted to interact with the zinc atom of the enzyme, and on the other hand on hydrophobic amino acids or analogs of same, which are adapted to interact with the hydrophobic site of the enzyme.

Preferred are dipeptides of phenylalanine and leucine. There may also be used dipeptides of phenylalanine with another hydrophobic amino acid, or leucine with another hydrophobic amino acid. There may also be used dipeptides based on other hydrophobic amino acids, such as isoleucine, tryptophan, valine, methionine and analogs of these.

There may also be used 2-mercaptoacyl tripeptides of phenylalanine, leucine and another hydrophobic amino acid, or 2-mercaptoacyl tripeptides based on any of the above hydrophobic amino acids.

In the dipeptides and in the tripeptides one of the amino acids may be a neutral amino acid, like alanine, serin or threonine. Although exemplified with reference to acetyl derivatives, it ought to be understood that other acyl groups may be used instead. Furthermore, there are exemplified two highly active 2-mercaptoacetyl dipeptides. Tripeptides which contain the dipeptide sequence of the two novel compounds are also active and are intended to be within the scope of the present invention. The 2-mercaptoacyl derivatives are highly active as inhibitors of elastase produced by *Pseudomonas aeruginosa*, and thus they are effective agents for the treatment of afflictions caused by this microorganism, and especially of *pseudomonas keratitis*.

The 2-mercaptoacetyl derivatives, and especially the 2-mercaptoacetyl derivatives mercaptoacetyl-L-phenylalanyl-L-leucine and 2-mercaptoacetyl-L-leucyl-L-phenylalanine inhibit effectively *P. aeruginosa* elastase.

It is advantageous to add a physiologically acceptable anti-oxidant which can be safely used in the environment where the bacteria causing the disease are present. Amongst suitable antioxidants there may be mentioned sodium metabisulfite.

It is also advantageous to add to certain formulations a suitable physiologically acceptable surfactant. Especially suitable are non-ionic surfactants. Such non-ionic surfactants are known in the art and are used in ophthalmic preparations.

The above mercaptoacyl derivatives effectively inhibit metalloendopeptidases, the activity of which depends on a zinc atom (which iis part of the effective site of the enzyme). The elastase of *Pseudomonas aeruginosa* belongs to this type of enzyme and experiments have shown these mercaptoacetyl derivatives to be effective agents in the prevention of damage by infections of this microorganism, and also as a curative agent, either by itself or in combination with antimicrobials, against infections of *Pseudomonas aeruginosa*. When an eye is infected by *Pseudomonas aeruginosa*, elastase is secreted by the microorganisms and this causes a rapid disintegration of the proteins of the cornea, this being frequently a non-reversible process which may lead to loss of sight of the afflicted eye.

The novel inhibitors of enzymes of this type can also be used effectively as curative or preventive agents in the case of afflictions by other microorganisms which secrete similar enzymes.

The invention is illustrated mainly with reference to *Pseudomonas aeruginosa*, but it ought to be understood that this is by way of example only and that other eye diseases involving attack by enzymes of this type can be treated with the novel compositions of the invention.

The preparation of representative 2-mercaptoacyl dipeptides, and specifically 2-mercaptoacetyl dipeptides is illustrated in the following. It ought to be understood that the acetyl group is illustrative and that other conventional acyl, and especially lower alkanoyl groups can be used instead in the molecule. Furthermore, as pointed out above, tripeptides which contain the sequence of the two amino acids of the above compounds are also effective inhibitors.

Dipeptide Methyl Ester Hydrochlorides

The N-hydroxysuccinimide ester method was used to synthesize Boc-Leu-Phe-OMe, $[\alpha]_D^{23} = -20.6°$ (cl, DMF), mp 86°–87° C.; Boc-Leu-D-Phe-Ome, $[\alpha]_D^{23} = -4.5°$ (cl, DMF), mp 104°–105° C.; Boc-Phe-Leu-OMe, $[\alpha]_D^{23} = -16.5°$ (cl, DMF), mp 107°–108° C.

The corresponding hydrochloride salts were prepared by removal of the Boc group with 2N HCl/acetic acid (2 ml/mmole) at room temperature for 15 min, followed by removal of the solvent in vacuo.

The hydrochlorides of Leu-Phe-OMe (1a, mp 197°–198° C.) and of Leu-D-Phe-OMe (1b, mp 218°–219° C.) were isolated by adding ether and filtering and were obtained in 98% yield. The hydrochloride of Phe-Leu-OMe (1c, mp 143°–144° C.; soften 135° C.) was crystallized by adding ether and removing it in vacuo, treating with petroleum ether and decantating, and then adding ether to the residue. The precipitated material was filtered and washed with ether. It was recrystallized by dissolving in ethanol/ether (3:10) and evaporation of the solvent, followed by the addition of ether. The yield was 66%. HPLC analysis of the compounds 1a, 1b and 1c revealed their purity (>98%).

S-Acetyl-2-Mercaptoacetic Acid N-Hydroxysuccinimide Ester

S-Acetyl-2-mercaptoacetic acid was obtained by reacting 10% molar excess of acetic anhydride with thioglycolic acid at room temperature for 4 days. The products were distilled under reduced pressure; the compound distilling at 115°–125° C. and 2–3 mm Hg was then collected.

Anal. Calculated for $C_4H_6SO_3$: S, 23.90. Found: S, 24.10.

S-Acetyl-2-mercaptoacetic acid (75 mmoles) and N-hydroxysuccinimide (75 mmoles), were dissolved in 150 ml dioxane and reacted with cooling in ice with N,N'-dicyclohexylcarbodiimide (75 mmoles) and the mixture was kept at 4° C. for 16 h. The N,N'-dicyclohexylurea formed was removed by filtration and the solvent evaporated in vacuo. The residue was twice recrystallized from 2-propanol.

Yield 66%, mp 94°–96° C.

Anal.: Calculated for $C_8H_9SNO_5$: N, 6.06; S, 13.87. Found: N, 6.12; S, 13.29.

S-Acetyl-2-Mercaptoacetyl Dipeptide Methyl Esters (2a, b, c)

The dipeptide methyl ester hydrochloride (12.5 mmoles of 1a, 1b or 1c) was dissolved in 30 ml DMF, the solution cooled in ice and N-ethyl-morpholine (1.75 ml) was added. The active S-acetyl-2-mercaptoacetic acid N-hydroxysuccinimide ester (12.5 mmoles) was then added and the solution kept at room temperature overnight. The solvent was removed in vacuo and the residue treated with 50 ml water. The precipitated material was dispersed in the water, then filtered and washed with cold water. The precipitate was crystallized twice from ethanol/water (1:2). The yields were between 62% and 72%. The physical properties of the compounds are given in Table 1.

2-Mercaptoacetyl Dipeptides (3a, b, c)

The S-acetyl-2-mercaptoacetyl dipeptide methyl ester (4 mmoles 2a, 2b or 2c) was dissolved in 20 ml methanol, 5 ml of 2.2N NaOH were added and the solution kept at room temperature for 2.5–3 h. The solvent was removed in vacuo, the residue dissolved in 10 ml water and the solution cooled in ice, then acidified with 4 ml of 6N HCl. The precipitated material was dispersed, filtered and washed with cold water. The compound was twice-crystallized from ethanol/water (2:5). The yields were between 52% and 75%. The physical properties of the compounds are given in Table 1. In addition, the thiol content of the compounds was estimated and the amino acid analysis determined. The thiol content, was 1.04, 0.99 and 0.99 mole SH per mole peptides 3a, 3b and 3c, respectively, and the Phe/Leu ratio was 1.01, 1.01 and 1.04, respectively. HPLC analysis of compounds 3a, 3b and 3c revealed their purity (>98% for 3a and 3b and >95% for 3c).

Inhibition Studies

Measurements were performed at 25° C. The reaction solutions (2.5 ml) ocnsisted of 0.1–0.2 mM substrate in 0.1M NaCl-0.05M Tris. HCl-0.01M $CaCl_2$, pH 7.5; all were demetallized. The hydrolysis of substrate was first order and rates were determined from plots of $(A_t - A)$ versus t ($A_t$ and A represent absorbance at time t and after completion of the reaction, respectively). Inhibition constants ($K_i$) were derived from plots of $k_o/k_i$ versus inhibitor concentration ($k_o$ and $k_i$ are the observed rate constants in absence and presence of inhibitors, respectively).

The inhibition characteristics of HS-Ac-Leu-Phe for Pseudomonas elastase, using furylacryloyl-Gly-Leu-Ala as the substrate, was determined. The $K_i$ values derived for the enzymes is 1.5 $\mu$M. The $K_i$ value for HS-Ac-Phe-Leu was 0.2 $\mu$M.

The inhibition by HS-Ac-Leu-Phe is stereospecific since HS-Ac-Leu-D-Phe is far poorer an inhibitor of the enzyme, $K_i = 34$ $\mu$M.

Protection of the Cornea

Damage to the cornea caused by Pseudomonas aeruginosa elastase can be prevented by the inhibitors of the present invention.

1. When about 1 $\mu$g of the pure elastase is injected into the cornea of a rabbit eye, the cornea "dissolves", swells and perforates within about an hour and a half from the time of the injection of the elastase. When the same amount of enzyme is injected in the presence of 0.2$\mu$ mole (70 $\mu$g) of the inhibitor mercaptoacetyl-L-phenylalanyl-L leucine, the dissolution effect is postponed to about 9 hours from the injection of the enzyme. The damage caused after this period of time is limited, and generally it does not affect more than about 10 percent of the cornea. The perforation of the cornea is prevented.

TABLE 1

| | | | Analytical data of 2-mercaptoacetyl dipeptides | | | | | | | |
|---|---|---|---|---|---|---|---|---|---|---|
| | | | | Analyses | | | | | | |
| | | $[\alpha]_D^{25}$ (c1, DMF) | Calculated | | | | % Found | | | |
| | mp (°C.) | degree | C | H | N | S | C | H | N | S |
| 2a Ac—S—CH$_2$—CO—Leu—Phe—OMe | 115–120 | −24.5 | 58.80 | 6.91 | 6.86 | 7.85 | 58.77 | 6.94 | 7.17 | 7.83 |
| 2b Ac—S—CH$_2$—CO—Leu—DPhe—OMe | 107–108 | +2.9 | " | " | " | " | 59.02 | 6.90 | 6.88 | 8.13 |
| 2c Ac—S—CH$_2$—CO—Phe—Leu—OMe | 110–111 | −18.2 | " | " | " | " | 58.70 | 6.85 | 6.90 | 7.88 |
| 3a HS—Ac—Leu—Phe | 158–159 | −19.4 | 57.93 | 6.86 | 7.95 | 9.10 | 58.00 | 6.83 | 8.07 | 8.67 |
| 3b HS—Ac—Leu—DPhe | 195–196 | +1.8 | " | " | " | " | 58.00 | 6.90 | 7.96 | 8.93 |
| 3c HS—Ac—Phe—Leu | 163–164 | −6.0 | " | " | " | " | 57.98 | 6.84 | 7.86 | 8.79 |

Ac—S—CH$_2$—CO—, S—acetyl-2-mercaptoacetyl-

2. When rabbit corneas were treated topically with a 10 mM solution of the inhibitor, (drops were applied one at a time every 15 minutes for an hour prior to the injection of the enzyme, and for an additional hour after enzyme injection, and then every half hour for 3 hours, and every hour for 5 additional hours) no "dissolution" of the cornea takes place at all. The appearance of the eye is entirely normal and it remains for many hours after the cessation of the treatment. This series of experiments proves that the mercaptoacetyl dipeptide is an effective agent preventing damage to the eye caused by Pseudomonas aeruginosa elastase.

3. The efficacy of combined treatment with antibiotics and the inhibitor HSAc-Phe-Leu was compared with that of the antibiotics alone using an experimental model of Pseudomonas keratitis in rabbit eyes. The inhibitor at a concentration of 10 mM was given, one drop at a time, every 15 min. for 1 hour after infection with the bacteria, and then hourly for additional 44 hours. The antibiotic (0.3% gentamicin sulfate) was applied every 2 hours, starting 16 hours after infection. The severity of the damage caused to the eyes that received the combination antibiotic plus inhibitor was significantly lower than that caused to the eyes that were treated with the antibiotic alone, meaning that the inhibitor HSAc-Phe-Leu had a protective effect also in the infection.

Thus, it is concluded that improved results can be obtained by a treatment combining the novel inhibitors together with conventional antibiotic. The antibiotic of choice is gentamycin sulfate. The novel inhibitor is advantageously applied periodically, such as hourly, to maintain a sufficient continuous concentration in the afflicted eye. The concentrations of the inhibitor can vary within wide limits such as 0.5 mg/ml to about 10 mg/ml, the preferred concentration being about 3.5 mg/ml (10 mM).

Further experiments were carried out. The schedule of topical treatment is set out in Table 2. The criteria applied to the results are set out in Table 3. Results are presented in Tables 4 and 5.

TABLE 2

Schedules for topical treatment of rabbit eyes infected with *Pseudomonas aeruginosa*

| Agent | Treatment Schedule | |
|---|---|---|
| | Expt. A | Expt. B |
| HS—Ac—Phe—Leu or PBS | Every 15 min for 2 hours and then every hour for additional 43 hours* | Every 20 min. for 1 hour and then every hour for additional 42 hours. |
| Gentamicin | Every 2 hours between 16 and 45 hours. | Every 2 hours, between 13 and 43 hours. |

*Time is expressed in hours after infection.

TABLE 3

Criteria for scoring the severity of ocular lesions in experimental *Pseudomonas keratitis*

| Reaction | Score |
|---|---|
| (a) Corneal abscess, up to 33% of the cornea | +1 |
| Corneal abscess, 34–66% of the cornea | +2 |
| Corneal abscess, 67–100% of the cornea | +3 |
| (b) Corneal melting, up to 33% of the cornea | +1 |
| Corneal melting, 34–66% of the cornea | +2 |
| Corneal melting, 67–100% of the cornea | +3 |
| (c) Corneal bulge, mild | +1 |
| Corneal bulge, severe | +2 |
| (d) Hypopyon, up to 3 mm | +1 |

TABLE 3-continued

Criteria for scoring the severity of ocular lesions in experimental *Pseudomonas keratitis*

| Reaction | Score |
|---|---|
| Hypopyon, 3 mm | +2 |
| (e) Perforation* | +10 |

*Maximum score (10).

TABLE 4

Clinical scores of rabbit eyes infected with *P. aeruginosa* and treated with PBS (group 1), gentamicin (group 2), or gentamicin plus HS—Ac—Phe—Leu (group 3).

| Treatment group | Eye No. | Clinical Scores | | | |
|---|---|---|---|---|---|
| | | 28 hours | | 48 hours | |
| | | Expt. A | Expt. B | Expt. A | Expt. B |
| (1) PBS (control) | 1 | 4 | 1 | 10 | 7 |
| | 2 | 4 | 4 | 6 | 7 |
| | 3 | 6 | 2 | 8 | 6 |
| | 4 | 3 | 5 | 6 | 5 |
| | 5 | 3 | 6 | 7 | 8 |
| | 6 | 10 | 10 | 10 | 10 |
| | 7 | 6 | 3 | 7 | 7 |
| | 8 | 7 | 5 | 6 | 7 |
| | 9 | 3 | | 5 | |
| (2) Gentamicin | 1 | 7 | 3 | 7 | 6 |
| | 2 | 4 | 2 | 10 | 7 |
| | 3 | 3 | 3 | 6 | 5 |
| | 4 | 6 | 2 | 6 | 4 |
| | 5 | 3 | 1 | 4 | 4 |
| | 6 | 1 | 1 | 3 | 4 |
| | 7 | 6 | 1 | 6 | 4 |
| | 8 | | 6 | | 5 |
| (3) Gentamicin plus HS—Ac—Phe—Leu | 1 | 1 | 1 | 7 | 4 |
| | 2 | 3 | 1 | 7 | 4 |
| | 3 | 4 | 1 | 6 | 3 |
| | 4 | 3 | 2 | 7 | 4 |
| | 5 | 1 | 5 | 5 | 6 |
| | 6 | 1 | 1 | 5 | 4 |
| | 7 | 1 | 1 | 3 | 3 |
| | 8 | | 1 | | 2 |
| | 9 | | 1 | | 3 |
| | 10 | | 1 | | 4 |

Statistical analysis by the $X^2$-test of the scores obtained 28 hours after infection showed that the scores of group 3 were significantly lower than those of both, group 1 and group 2 (p 0.01). At forty eight hours after infection, the differences between the scores of the various groups were found insignificant.

TABLE 5

Corneal melting in rabbit eyes infected with *P. aeruginosa* and treated with PBS (group 1), gentamicin (group 2) or gentamicin plus HS—Ac—Phe—Leu (group 3).

| Treatment group | Time after infection (h) | Development of corneal melting[a] | Development of extensive[b] corneal melting |
|---|---|---|---|
| (1) PBS | 28 | 16/17 (94) | 8/17 (47) |
| | 48 | 16/17 (94) | 14/17 (82) |
| (2) Gentamicin | 28 | 11/15 (73) | 4/15 (27) |
| | 48 | 14/15 (93) | 9/15 (60) |
| (3) Gentamicin plus HS—Ac—Phe—Leu | 28 | 5/17 (29) | 0/17 (0) |
| | 48 | 17/17 (100) | 5/17 (29) |

[a]No. of eyes with melting/No. of eyes in group (%)
[b]30% of corneal area affected.

We claim:

1. An ophthalmic pharmaceutical composition for the treatment of afflictions of the eye caused by metalloendopeptidases, which comprises an ophthalmically acceptable carrier containing 2-mercaptoacetyl L-phenylalanyl-L-leucine and gentamicin.

2. The composition of claim 1, wherein the 2-mercaptoacetyl L-phenylalanyl-L-leucine is incorporated in an amount of from 1 mmole to 10 mmoles per liter of the composition.

3. The composition of claim 1, additionally incorporating a physiologically acceptable antioxidant.

4. The composition of claim 3, wherein the antioxidant is sodium metabisulfite.

5. The composition of claim 1, additionally incorporating a physiologically acceptable surfactant.

6. The composition of claim 5, wherein the surfactant is a nonionic surfactant.

7. A process for the treatment of Pseudomonas keratitis and for preventing damage to the eye caused by *P. aeruginosa* elastase, which comprises applying to the eye an effective quantity of 2-mercaptoacetyl L-phenylalanyl-L-leucine as an inhibitor for *P. aeruginosa* elastase, and gentamicin as an antibiotic.

8. The process of claim 7, wherein the 2-mercaptoacetyl L-phenylalanyl-L-leucine is applied to the eye in an ophthalmic preparation in an amount of from 1 mmole to 10 mmoles per liter thereof.

9. The process of claim 7, wherein the 2-mercaptoacetyl L-phenylalanyl-L-leucine is applied to the eye in an ophthalmic preparation additionally containing an antioxidant.

10. The process of claim 9, wherein the antioxidant is sodium metabisulfite.

11. The process of claim 7, wherein the 2-mercaptoacetyl L-phenylalanyl-L-leucine is applied to the eye in an ophthalmic preparation additionally containing a surfactant.

12. The process of claim 11, wherein the surfactant is a nonionic surfactant.

* * * * *